US010912588B1

(12) United States Patent
Klein, Jr. et al.

(10) Patent No.: US 10,912,588 B1
(45) Date of Patent: Feb. 9, 2021

(54) SUPER WING BOLT

(71) Applicant: New Standard Device, LLC, San Antonio, TX (US)

(72) Inventors: C. Douglas Klein, Jr., Andover, MA (US); Bryant T. Phamvu, San Antonio, TX (US); Robert E. Wigginton, McKinney, TX (US)

(73) Assignee: New Standard Device, LLC, San Antonio, TX (US)

( * ) Notice: Subject to any disclaimer, the term of this patent is extended or adjusted under 35 U.S.C. 154(b) by 0 days.

(21) Appl. No.: 17/029,217

(22) Filed: Sep. 23, 2020

Related U.S. Application Data

(62) Division of application No. 16/406,224, filed on May 8, 2019.

(51) Int. Cl.
*A61B 17/64* (2006.01)
*F16B 37/08* (2006.01)

(52) U.S. Cl.
CPC ........ *A61B 17/645* (2013.01); *A61B 17/6408* (2013.01); *A61B 17/6425* (2013.01); *F16B 37/08* (2013.01)

(58) Field of Classification Search
CPC ............ A61B 17/6408; A61B 17/6425; A61B 17/6433; A61B 17/645; F16B 37/08; F16B 37/16; F16B 7/18; F16B 23/0092; F16B 39/282
See application file for complete search history.

(56) References Cited

U.S. PATENT DOCUMENTS

| | | | |
|---|---|---|---|
| 1,393,459 A | 10/1921 | Smith | |
| D274,979 S | 8/1984 | Hill | |
| 4,482,368 A | 11/1984 | Roberts | |
| D302,243 S | 7/1989 | Gonzalez | |
| D672,639 S | 12/2012 | Pawluk | |
| 8,343,166 B2 * | 1/2013 | Maughan | A61B 17/6466 606/105 |
| 9,903,408 B2 * | 2/2018 | Liao | F16B 37/0821 |
| 2020/0122306 A1 * | 4/2020 | Hu | B25B 27/023 |

FOREIGN PATENT DOCUMENTS

| | | |
|---|---|---|
| CN | 204628222 | 9/2015 |
| CN | 108397471 | 8/2018 |
| DE | 3633041 | 6/1988 |
| DE | 9315399 | 2/1994 |

(Continued)

OTHER PUBLICATIONS

Griffith, "Wingnuts," downloaded from <http://www.classiclightweights.co.uk/components/wingnuts-griffith-comp.html> in Dec. 2018.

(Continued)

*Primary Examiner* — Pedro Philogene
(74) *Attorney, Agent, or Firm* — Gregory K. Goshorn; Greg Goshorn, P.C.

(57) ABSTRACT

Provided is a super wing nut bolt. The super wing bolt comprises a head, two wings that extend transversely from opposite sides of the head, a tightening hole that passes perpendicular through the head between the two wings, a tightening slot in a first top surface of the head, a polygonal-sided shaft that extends downward from the head and a threaded hole that passes axially through the shaft.

6 Claims, 7 Drawing Sheets

(56) References Cited

FOREIGN PATENT DOCUMENTS

DE           9415134      12/1994
GB           GB178448     7/1923
IT           1248502      1/1995

OTHER PUBLICATIONS

Vintage Bike Shed, "N0s pair of 1930-50s vintage chromed wing nuts,⅜" thread,with serrated washers," downloaded from <https://www.ebay.co.uk/itm/N0S-PAIR-OF-1930-50s-VINTAGE-CHROMED-WING-NUTS-3-8-THREAD-WITH-SERRATED-WASHERS-1283240430976> in Dec. 2018.
Soua,"Pair Bike 5/16 inch Front Axle Wing Nuts Soua Vintage," downloaded from <https://www.ebay.ca/itm/Classic-nuts-SOUA-for-Vintage-BIKE-suit-Peugeot-Mercier-Gitane-MBK-4303126406260?hash=item4693bde474> on Oct. 27, 2020.
H, "Vintage Bike Bicycle Hub ⅜ Wing Nuts New Wheel Wingnuts Wing Nut Wingnut", downloaded from <https://www.ebay.ca/itm/VINTAGE-BIKE-BICYCLE-HUB-3-8-WING-NUTS-NEW-WHEEL-WINGNUTS-WING-NUT-NINGNUT/301773095556?hash=item4643140284:g:75MAAOSw5VFWHY39:rk:3:pf:0> on Oct. 27, 2020.
Vintage Bike Shed, "New Old Stock Vintage Gripfast Chromed Rear Wing Nuts,with Serrated Washers,⅜" downloaded from <https://picclick.co.uk/New-Old-Stock-Vintage-Gripfast-Chromed-Rear-Wing-283101169211.html> on Oct. 27, 2020.

\* cited by examiner

SUPER WING BOLT

CROSS-REFERENCES TO RELATED APPLICATIONS

The present application is a Divisional and claims the benefit of the filing date of an application entitled, "Super Wing Nut" Ser. No. 16/406,224, filed May 8, 2019, assigned to the assignee of the present application, and herein incorporated by reference.

FIELD OF THE DISCLOSURE

The claimed subject matter relates generally to novel bolts and, more specifically, to bolts that include a head that facilitates both loosening and tightening the bolt, primarily with respect to an orthopedic fixation device.

BACKGROUND

External Bone Fixation devices are employed by Orthopedic Health Care Providers to treat bone deformity and acute trauma. Such devices are typically assembled from components fastened together using, among other components, nuts and bolts. Speed of assembly is often desirable, particularly in the event of trauma, yet the currently available nuts and bolts typically require the use of specific wrenches and other tools to be install, spin and tighten onto a corresponding bolt or nut, respectively.

External Fixation Devices may include variously configured plates and posts. Plates are fastened together with struts with a threaded portion, the threaded portion secured to plate by a nut. A post may have a threaded hole that enables the post to be attached to a plate or another post with a bolt.

SUMMARY

Provided are super bolts that include a novel head that tenable the bolts to be attached for their intended purposes more easily and quickly. As the Inventors herein have realized, External Bone Fixation (EBF) devices would benefit from novel nuts and bolts that weigh less and are able to be assembled more quickly with a fewer number and wider variety of tools than typical nuts and bolts. In other words, there is a need for nuts and bolts that are lighter, faster and easier to assemble, particularly with respect to EBF devices.

Provided is a fastener for use with a correspondingly threaded bolt comprising a head, two wings that extend transversely from opposite sides of the head, a tightening hole that passes perpendicular through the head between the two wings, a tightening slot in a top surface of the head, a polygonal sided shaft that extends downward from the head and a threaded hole that passes axially through the shaft.

Also provided is a fastener for use with a correspondingly threaded nut comprising a head, two wings that extend transversely from opposite sides of the head, a tightening hole that passes perpendicular through the head between the two wings, a tightening slot in a top surface of the head, a polygonal sided shaft that extends downward from the head and a threaded shaft that extends downward from the polygonal sided shaft.

Also provided is a two-part fastener with a first part comprising a head, two wings that extend transversely from opposite sides of the head, a tightening hole that passes perpendicular through the head between the two wings; a tightening slot in a top surface of the head, a polygonal sided shaft that extends downward from the head, and a threaded shaft that extends downward from the polygonal sided shaft. The second part comprises a head, two wings that extend transversely from opposite sides of the head, a tightening hole that passes perpendicular through the head between the two wings, a tightening slot in a first top surface of the head, a polygonal sided shaft that extends downward from the head, and a threaded hole that passes axially through the shaft, wherein the threaded shaft of the second part threads through the threaded hole of the first part.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures, in which:

DETAILED DESCRIPTION OF THE FIGURES

Although described with particular reference to an External Bone Fixation device, the claimed subject matter can be implemented in any mechanical application in which ease and speed of assembly is desirable. Those with skill in the relevant arts will recognize that the disclosed embodiments have relevance to a wide variety of situation in addition to those described below.

Figure 1:
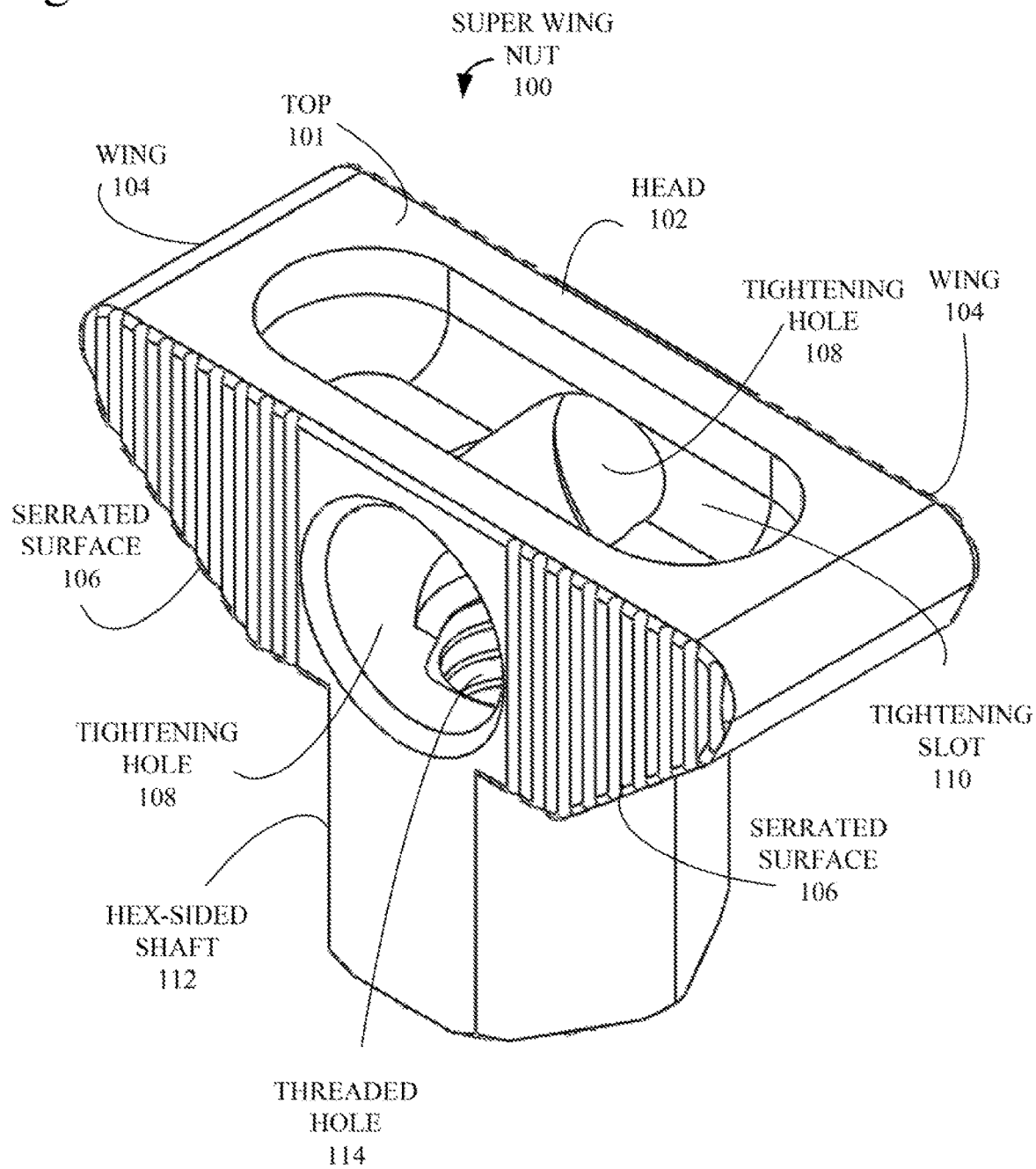
FIG. 1 is an illustration of super wing nut with a novel head in accordance with the claimed subject matter.

FIG. 1 is an illustration of super wing nut 100 constructed in accordance with the claimed subject matter. A head 102 of nut 100 includes two wings 104, each wing including a serrated surface 106 that are parallel to each other along the sides of head 102. A surface 101 is referred to as the "top" of super wing nut 100 and head 102. Although not visible in FIG. 1, the side of each wing 104 opposite serrated surfaces 106 also has a serrated surface. Wings 104 provide a first means to either loosen or tighten wing nut 100 by enabling wing nut 100 to be rotated, typically with a user's ringers but also with a wrench if necessary. A tightening hole 108 runs through head 102 perpendicular to serrated surfaces 106 of wing nut 100. Tightening hole 108 serves two (2) purposes, the first is to lighten the weight of wing nut 100 and the second to provide a second means to either loosen or tighten wing nut 100 by inserting a rod (not shown) or other implement into hole 108 and rotating head 102 of wing nut 100. A tightening slot 110 is positioned on the top of head 102 and also serves two (2) purposes, the first to lighten the weight of wing nut 100 and the second is to provide a third means to either loosen or tighten wing nut 100, for example by using a screwdriver (not shown) or other implement inserted into tightening slot 110.

A lower portion of wing nut 100 includes a polygonal sided shaft, which in this illustration is six-sided, or hex-sided, shaft 112 that provides a fourth means to loosen or tighten wing nut 100 by using an appropriately sized wrench (not shown). Running axially through the center of the length of shaft 112 is a threaded hole 114 into which a matching bolt would be threaded. Either a typical bolt or a super bolt 200 (see FIGS. 4-6) may be used. Typically, the diameter of threaded hole 114 would he less than the diameter of both tightening hole 108 and tightening slot 110 so that a bolt threaded through threaded hole 114 of wing nut 100 would he able to extend through and out the top of head 102 if necessary.

Figure 2:
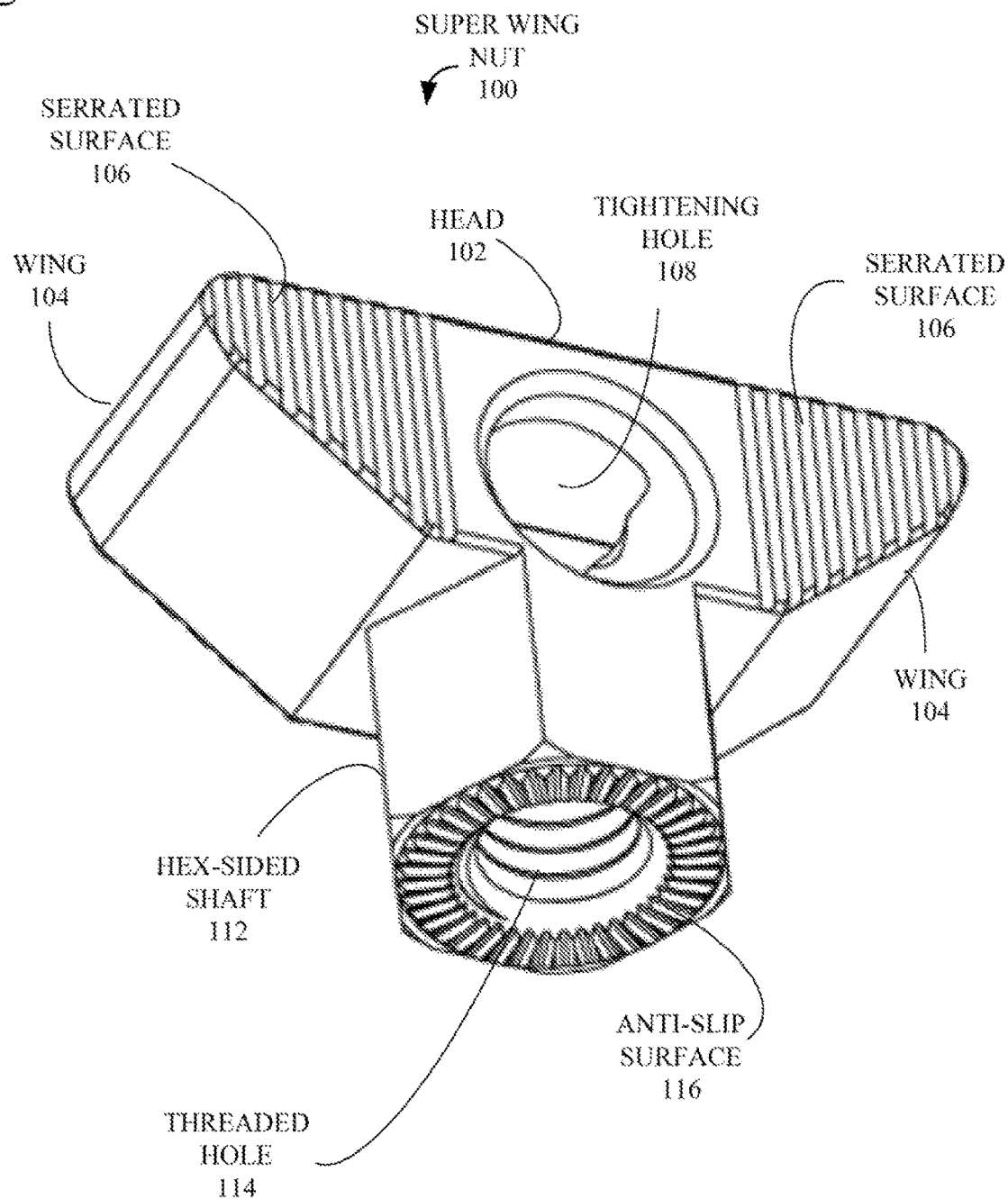
FIG. 2 is an illustration of the super wing nut of FIG. 1, from a different perspective, showing features that are obscured in the illustration of FIG. 1.

FIG. 2 is an illustration of the super wing nut 100 of FIG. 1, from a different perspective, showing additional features that are obscured in the illustration of FIG. 1. Head 102, wings 104, serrated surfaces 106, tightening hole 108, hex-sided shaft 112, and threaded hole 114, all introduced above in conjunction with FIG. 1, are shown. In addition, an anti-slip surface 116 is shown on the bottom of hex-sided shaft 112. Anti-slip surface 116 prevents wing nut 100 from loosening once wing nut 100 is tightened to a bolt or strut (see 310, FIG. 7). Typically, anti-slip surface would abut whatever component (see 302, 304, 306 and 308, FIG. 7) to which the strut or bolt are attached.

Figure 3:
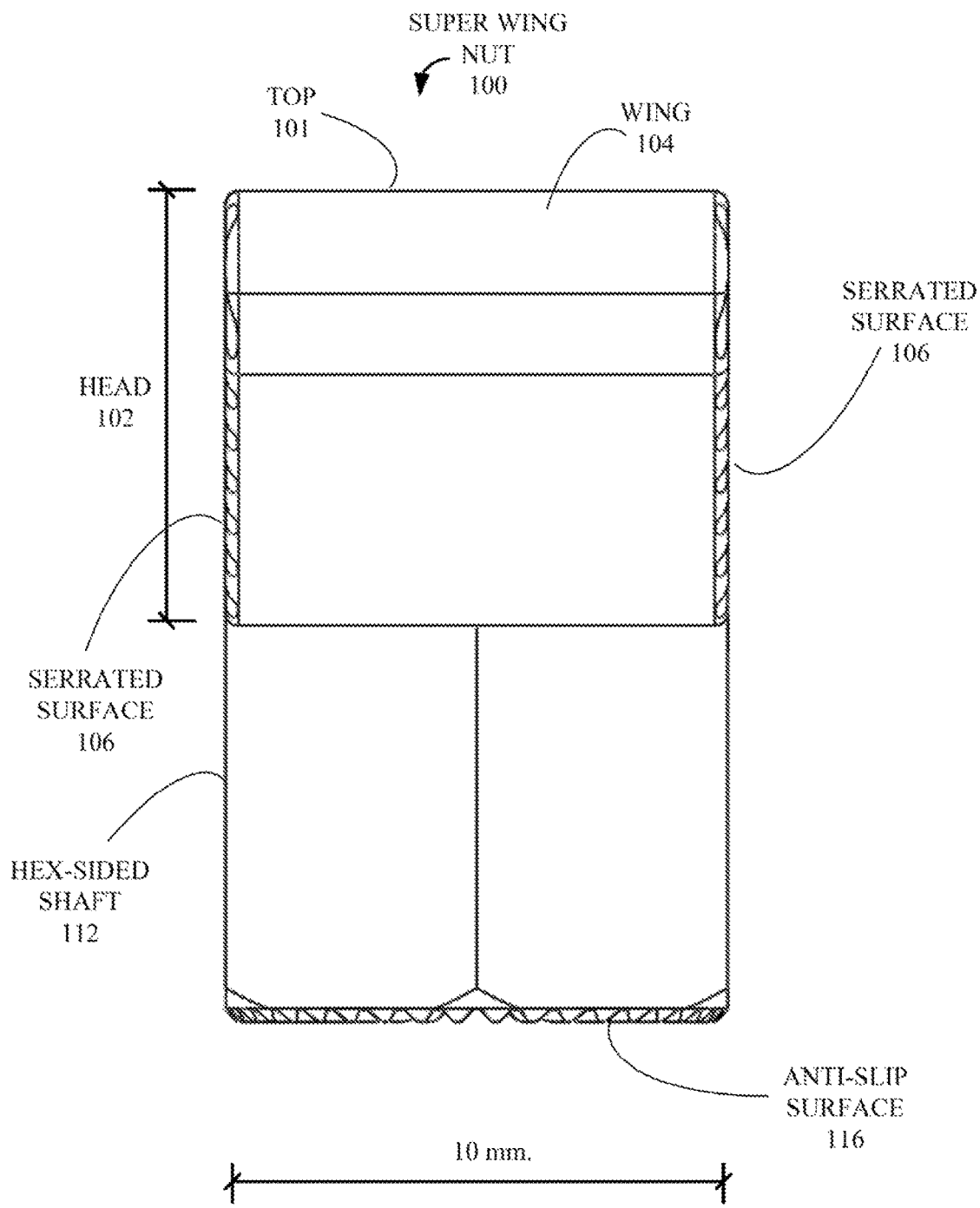
FIG. 3 is an illustration of the super wing nut of FIGS. 1 and 2, from a third perspective.

FIG. 3 is an illustration of the super wing nut 100 of FIGS. 1 and 2, from a third, or side, perspective. Visible in FIG. 3 are top 101, wing 104, serrated surface 106 and hex-sided shaft 112 introduced above in conjunction with FIGS. 1 and 2. The portion of super wing nut 100 referred to as head 102 is also illustrated. Also visible is anti-slip surface 116, which was introduced above in conjunction with FIG. 2. FIG. 3 shows wing nut 100 with a width of ten millimeters (10 mm.), which would he a typical size when wing nut 100 is employed in conjunction with and external bone fixation device (see 300, FIG. 7). In this size wing nut 100, threaded hole 114 (FIGS. 1 and 2), which is not visible in FIG. 3, would typically be six millimeters (6 mm.). It should be understood that the illustrated sizes are only examples and the disclosed technology may be employed with wing nuts 100 of any size, both larger and smaller. In this embodiment, hex-sided shaft 112 has the same width as head 102 and two sides of shaft 112 are parallel to wings 104, which enables a single sized wrench to be used on either component 104 or 112 to loosen or tighten wing nut 100. In this example, the width of both wings 104 and shaft 112 are ten-millimeter (10 mm.) and a ten-millimeter wrench (not shown) could be employed to either tighten or loosen wing nut 100 by applying the wrench to either wings 104 or shaft 112.

Figure 4:
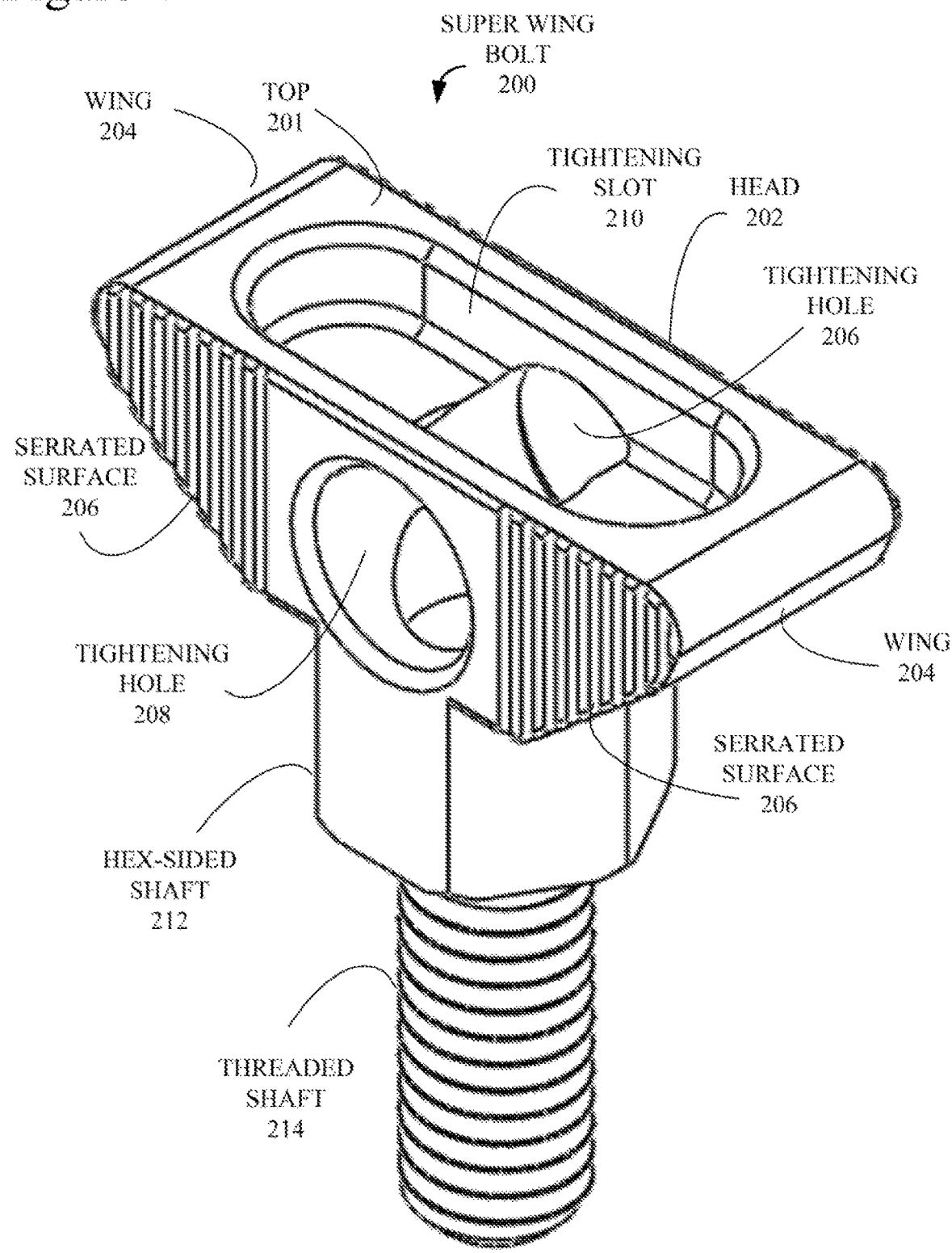
FIG. 4 is an illustration of super wing bolt with a novel head in accordance with the claimed subject matter.

FIG. 4 is an illustration of super wing bolt 200 with a novel head in accordance with the claimed subject matter. A head 202 of bolt 200 includes two wings 204, each wing including a serrated surface 206 that are parallel to each other along the sides of head 202. A surface 201 is referred to as the "top" of super wing bolt 200 and head 202. Although not visible in FIG. 4, the side of each wing 204 opposite serrated surfaces 206 also has a serrated surface. Wings 204 provide a first means to either loosen or tighten wing bolt 200 by enabling wing bolt 200 to be rotated, typically with a user's fingers but also with a wrench if necessary. A tightening hole 208 runs through head 202 perpendicular to serrated surfaces 206 of wing bolt 200. Tightening hole 208 serves two (2) purposes, the first is to lighten the weight of wing bolt 200 and the second to provide a second means to either loosen or tighten wing bolt 200 by inserting a rod (not shown) or other implement into hole 208 and rotating head 202 and wing bolt 200. A tightening slot 210 is positioned on the top of head 202 and also serves two (2) purposes, the first to lighten the weight of wing bolt 200 and the second is to provide a third means to either loosen or tighten wing bolt 200, for example by using a screwdriver (not shown) or other implement inserted into tightening slot 210.

A lower portion of wing bolt 200 includes a polygonal-sided shaft 212, which in this illustration is six-sided, or hex-sided, that provides a fourth means to loosen or tighten wing bolt 200 by using an appropriately sized wrench (not shown). Extending from the bottom of shaft 212 is a threaded shaft 214 onto which a matching nut would he threaded. Either a typical nut or super nut 100 (FIGS. 1-3) may be used.

Figure 5:
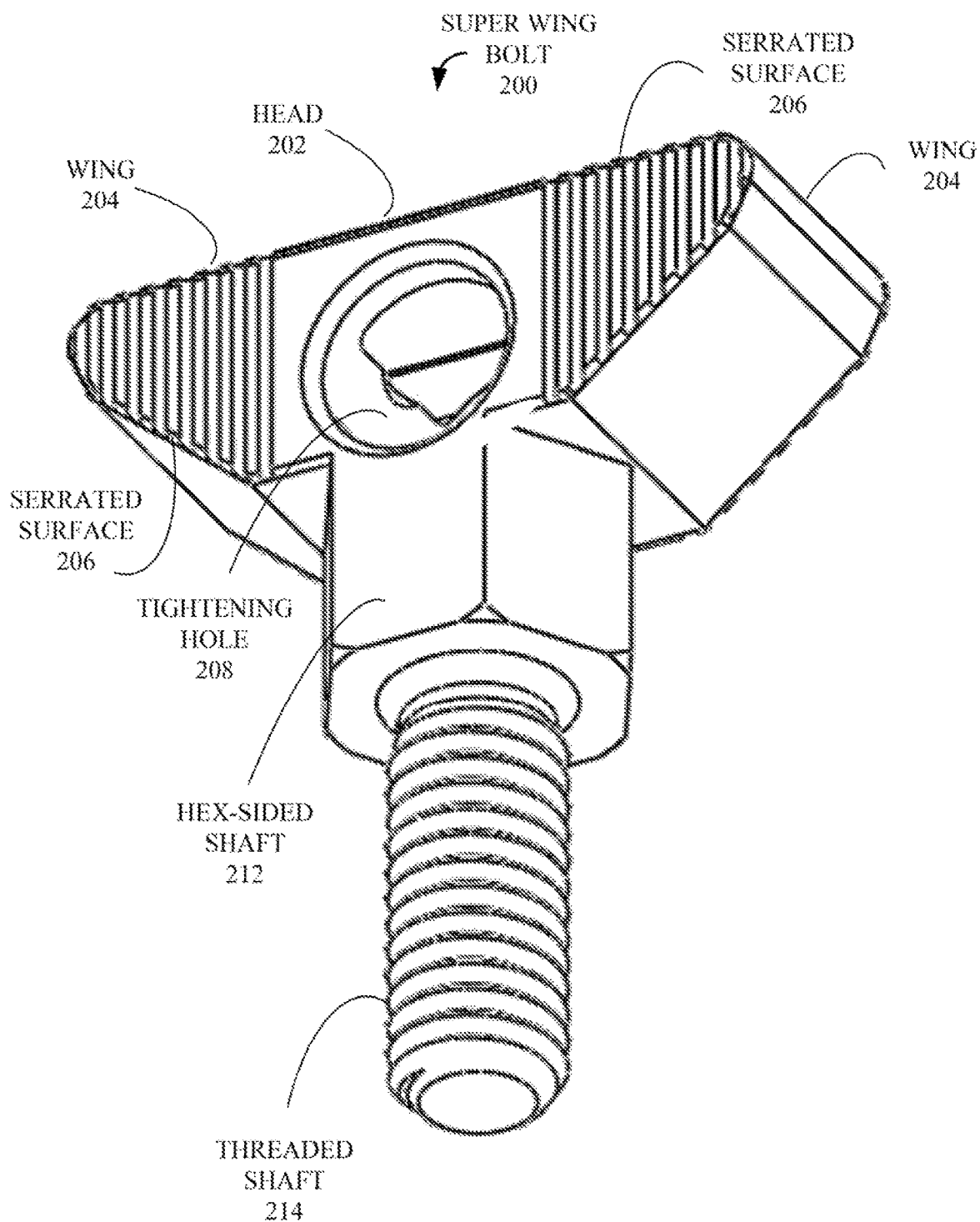
FIG. 5 is an illustration of the super wing bolt of FIG. 4, from a different perspective.

FIG. 5 is an illustration of the super wing bolt 200 of FIG. 4, from a different perspective. Head 202, wings 204, serrated surfaces 206, tightening hole 208, hex-sided shaft 212, and threaded shaft 214, all introduced above in conjunction with FIG. 4, are shown. Although an anti-slip surface such anti-slip surface 116 (FIGS. 2 and 3) is not shown on the bottom of hex-sided shaft 212, another embodiment may have such a surface.

Figure 6:
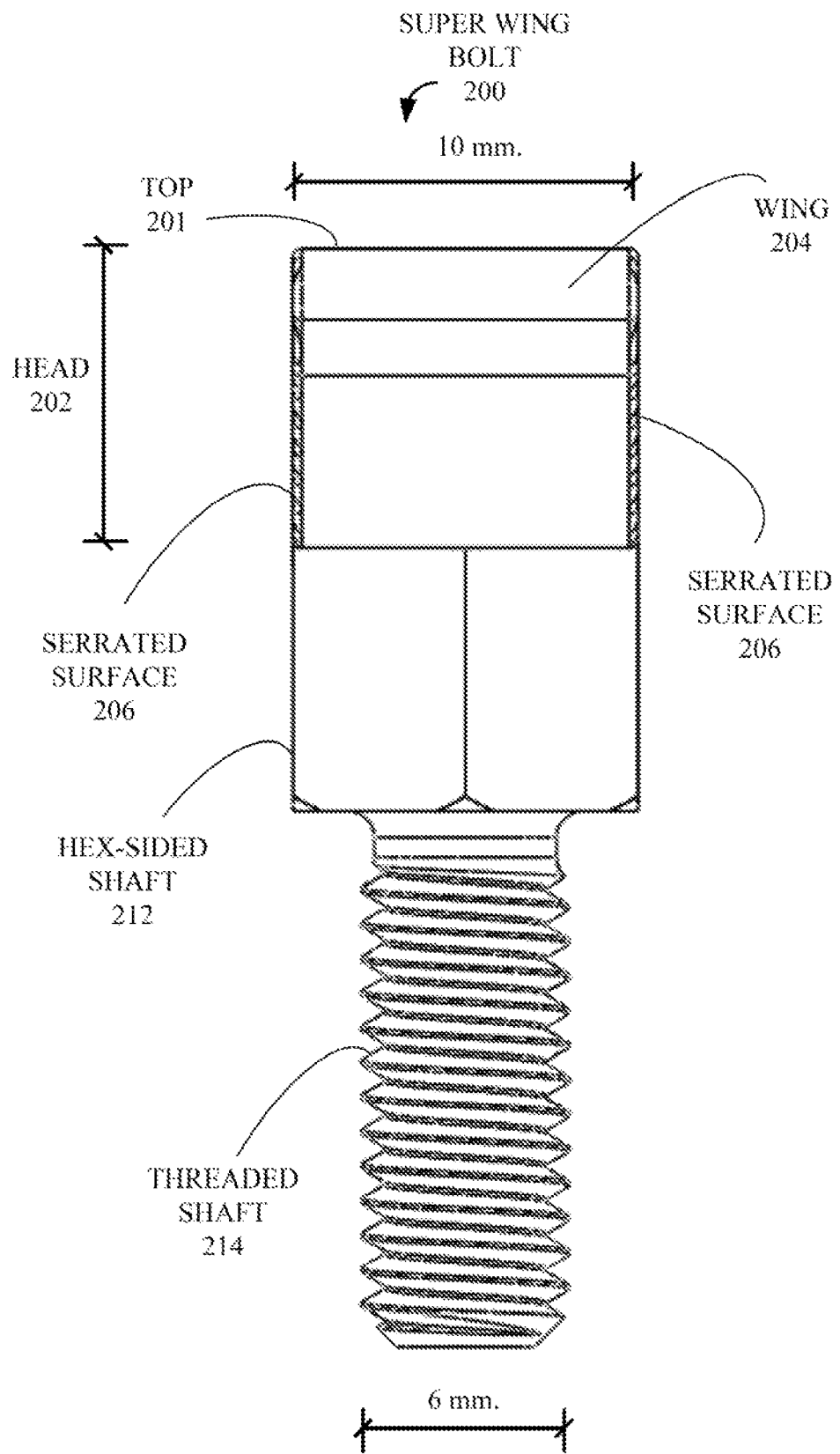
FIG. 6 is an illustration of the super wing bolt of FIGS. 4 and 5, from a third perspective.

FIG. 6 is an illustration of the super wing bolt 200 of FIGS. 4 and 5, from a third perspective. Visible in FIG. 6 are top 201, wing 204, serrated surface 206, hex-sided shaft 212 and threaded shaft 214, all introduced above in conjunction with FIGS. 4 and 5. The portion of super wing bolt 200 referred to as head 202 is also illustrated. FIG. 6 shows wing bolt 200 with a width of ten millimeters (10 mm.), which would be a typical size when wing bolt 200 is employed in conjunction with and external bone fixation device (see 300, FIG. 7). In this size wing bolt 200, threaded shaft 214 (FIGS. 4 and 5), would he six millimeters (6 mm.). It should be understood that the illustrated sizes are only examples and the disclosed technology may be employed with wing bolts 200 of any size, both larger and smaller. In this embodiment, hex-sided shaft 212 has the same width as head 202 and two sides of shaft 212 are parallel to wings 204, which enables a single sized wrench to be used on either component 204 or 212 to loosen or tighten wing bolt 200. In this example, the width of both wings 204 and shaft 212 are ten-millimeter (10 mm.) and a ten-millimeter wrench (not shown) could be employed to either tighten or loosen wing bolt 200 by applying the wrench to either wings 204 or shaft 212.

Figure 7:
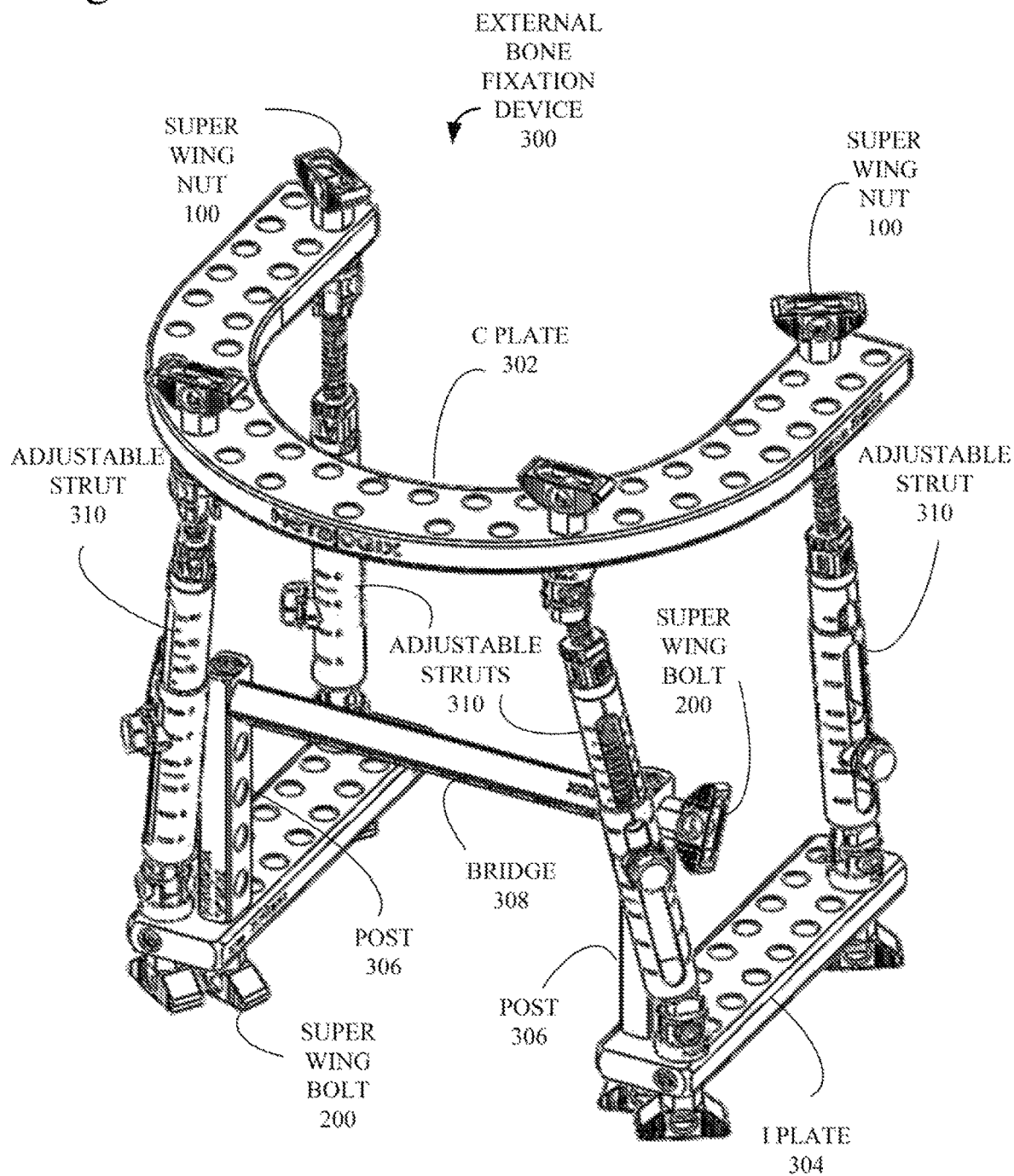
FIG. 7 is an illustration of an External Bone Fixation device that has been assembled with the nuts and bolts of FIGS. 1-6.

FIG. 7 is an illustration of an External Bone Fixation (EBF) device 300 that has been assembled with the wing nuts 100 (FIGS. 1-3) and wing bolts 209 (FIGS. 1-6). EBF device 300 includes a C-shaped Plate 302, two (2) I-shaped Plate 304, only one of which is labeled, posts 306 and a bridge 308. It should he understood that EBF device 300 is only one simple example and that a typical EBF device may include both additional components like those illustrated and addition types of components. C-shaped plate 302 is attached to I-shaped plates 304 by means of four (4) adjustable struts 310, only three (3) of which are labeled. Although not visible, adjustable struts 310 have a threaded shaft at each end that pass through holes in either C-shaped plate 302 or I-shaped plate 304. Super wing nuts 100 are threaded onto these shafts to secure adjustable struts 302 to their respective components 302 or 304. In this figure, only two wing nuts 100 are labeled, both of which are attaching adjustable struts 310 to C-shaped plate 302.

Although not visible, posts 306 have threaded holes that enable posts 306 to he affixed to I-shaped plates 304 by means of wing bolt 200, only one of which is labeled, by passing threaded shaft 214 through a hole in plates 304 into the threaded hole and tightening. In a similar fashion, threaded holes, which are not visible, at each end of bridge 308 enable bridge 308 to be affixed to posts 306 by passing threaded shaft 214 through a hole in post 306 and threading and tightening wing bolt 200.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements.

We claim:

1. A fastener, comprising:
a head;
two wings that extend transversely from opposite sides of the head;
a tightening hole that passes perpendicular through the head between the two wings;
a tightening slot in a top surface of the head;
a polygonal-sided shaft that extends downward from the head; and
a threaded shaft that extends downward from the polygonal sided shaft.

2. The fastener of claim 1, further comprising serrated surfaces on the two wings.

3. The fastener of claim 1, further comprising an anti-slip surface on the bottom of the polygonal-sided shaft.

4. The fastener of claim 1, wherein the polygonal-sided shaft is six sided.

5. The fastener of claim 1, wherein the polygonal-sided shaft is four sided.

6. The fastener of claim 1, wherein the width of the polygonal-shaft is equal to the width of the pair of wings and two sides of the polygonal-sided shaft are parallel to the pair of wings.

* * * * *